US012731665B2

(12) United States Patent
Vats et al.

(10) Patent No.: US 12,731,665 B2
(45) Date of Patent: Sep. 8, 2026

(54) SYSTEMS AND METHODS FOR PREDICTIVE ANALYSES WITH MACHINE LEARNING SYSTEMS

(71) Applicant: Optum, Inc., Minnetonka, MN (US)

(72) Inventors: Prashant Kumar Vats, Greater Noida West (IN); Rakshit Varma, Noida (IN)

(73) Assignee: Optum, Inc., Minnetonka, MN (US)

( * ) Notice: Subject to any disclaimer, the term of this patent is extended or adjusted under 35 U.S.C. 154(b) by 122 days.

(21) Appl. No.: 18/581,701

(22) Filed: Feb. 20, 2024

(65) Prior Publication Data

US 2025/0266140 A1 Aug. 21, 2025

(51) Int. Cl.

| | |
|---|---|
| ***G16H 20/10*** | (2018.01) |
| ***G06F 18/231*** | (2023.01) |
| ***G06F 40/295*** | (2020.01) |
| ***G16H 10/60*** | (2018.01) |
| ***G16H 15/00*** | (2018.01) |
| ***G16H 50/20*** | (2018.01) |

(52) U.S. Cl.
CPC ........... *G16H 15/00* (2018.01); *G06F 18/231* (2023.01); *G06F 40/295* (2020.01); *G16H 50/20* (2018.01)

(58) Field of Classification Search
CPC ........ G16H 15/00; G16H 50/20; G16H 50/30; G16H 50/70; G06F 18/231; G06F 40/295; G06F 40/30
See application file for complete search history.

(56) References Cited

U.S. PATENT DOCUMENTS 10,978,176 B2 4/2021 Cha et al.
11,468,998 B2 * 10/2022 Koblick ............... G06N 3/0985
2021/0118559 A1 4/2021 Lefkofsky
2022/0093261 A1 3/2022 Noshay et al.
2024/0087705 A1 * 3/2024 Etra ....................... G16H 20/70
2024/0120057 A1 * 4/2024 Gnanasambandam ...................... G16H 50/30

* cited by examiner

*Primary Examiner* — Maroun P Kanaan

(74) *Attorney, Agent, or Firm* — Bookoff McAndrews, PLLC

(57) ABSTRACT

A method includes receiving, by one or more processors, a dataset including transition data and factor data. The method includes generating a feature for a machine learning model based on the transition data, generating, via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction. The method further includes initiating performance of one or more remedial or analytical actions in response to generating the one or more data objects indicative of the transition prediction.

20 Claims, 7 Drawing Sheets

Figure 2:
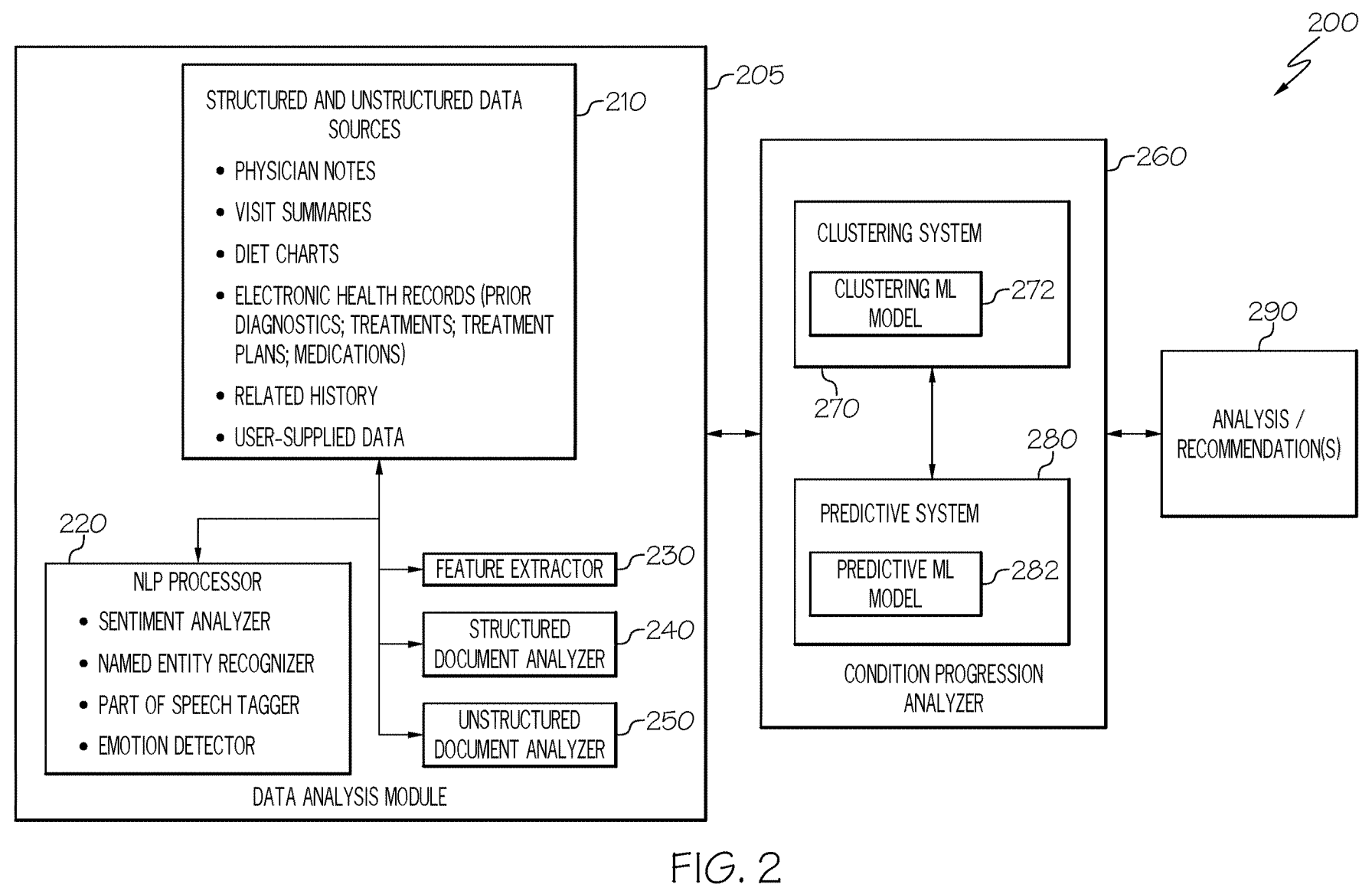

200

205

210

STRUCTURED AND UNSTRUCTURED DATA SOURCES

- PHYSICIAN NOTES
- VISIT SUMMARIES
- DIET CHARTS
- ELECTRONIC HEALTH RECORDS (PRIOR DIAGNOSTICS; TREATMENTS; TREATMENT PLANS; MEDICATIONS)
- RELATED HISTORY
- USER-SUPPLIED DATA

220

NLP PROCESSOR

- SENTIMENT ANALYZER
- NAMED ENTITY RECOGNIZER
- PART OF SPEECH TAGGER
- EMOTION DETECTOR

230 FEATURE EXTRACTOR

240 STRUCTURED DOCUMENT ANALYZER

250 UNSTRUCTURED DOCUMENT ANALYZER

DATA ANALYSIS MODULE

260

270 CLUSTERING SYSTEM

272 CLUSTERING ML MODEL

280 PREDICTIVE SYSTEM

282 PREDICTIVE ML MODEL

CONDITION PROGRESSION ANALYZER

290 ANALYSIS / RECOMMENDATION(S)

In [2]:
```
import nltk
from nltk.sentiment.vader import SentimentIntensityAnalyzer
```

In [3]:
```
# Create a SentimentIntensityAnalyzer object
sia = SentimentIntensityAnalyzer()
```

In [4]:
```
Def calc_polarity_score(notes):
    # split the notes into individual sentences
    sentences = nltk.sent_tokenize(notes)

    # Initialize a list to store the polarity scores for each sentence
    polarity_scores = [ ]

    # Loop through each sentence and get the polarity score
    for sentence in sentences:
        polarity_scores.append (sia.polarity_scores(sentence))

    # Calculate the average polarity score for all sentences
    average_polarity = sum([score['compound'] for score in polarity_scores]) / len(po:

    return average_polarity
```

In [5]:
```
# Read in the clinical notes for the patient
with open ('clinical_notes_negative.txt', 'r') as f:
    nnotes = f.read( )
```

In [6]:
```
nnotes
```

Out [6]:
```
"Patient is a 72-year-old female with a history of hypertension and chronic kidney di
sease. She presents today with complaints of decreased energy and mild shortness of b
reath. Laboratory results show a creatinine level of 3.2 mg/dL and GFR of 15 mL/mi
n/1.73m^2. Patient reports occasional non-adherence to her medication regimen, includ
ing lisinopril and amlodipine for hypertension control and cinacalcet for hyperparath
yroidism. The patient's blood pressure was noted to be 140/90 mmHg at the time of the
visit. The patient has been reminded of the importance of taking her medications as p
rescribed and maintaining a healthy diet and exercise routine. The patient will conti
nue to be monitored for progression of her chronic kidney disease and potential compl
ications. Overall, it can be noted that the patient's condition seems to be slightly
worse than her previous visit, the creatinine level and GFR have increased and the pa
tient's non-adherence to medication and lack of diet control could be contributing fa
ctors./n
```

502

In [7]:
```
print ("Average Polarity Score (Negative review) = ", calc_polarity_score(nnotes))
Average Polarity Score (Negative review) = -0.011587499999999994
```

Out [9]: "Patient is a 55-year-old male with a history of hypertension and chronic kidney di sease. He presents today with complaints of mild fatique.Laboratory results show a cre atinine level of 1.8 mg/dL and GFR of 45 mL/mi n/1.73m^2. Patient reports good adher ence to his medication regimen, including lisinopril and benazepril for hypertension control and erythropoietin for anemia. The patient's blood pressure was noted to be 1 30/80 mmHg at the time of the visit. The patient has been commended for his good cont rol of his blood pressure and adherence to his medications. The patient has been remi nded of the importance of maintaining a healthy diet and exercise routine. The patien t will continue to be monitored for progression of his chronic kidney disease and pot ential complications. Overall, it can be noted that the patient's condition seems to be stable and well-controlled. The creatinine level and GFR are within normal limits and the patient's good adherence to medication control and diet contol are likely contributi ng factors."

504

In [10]:
```
print ("Average Polarity Score (Positive review) = ", calc_polarity_score(pnotes))
Average Polarity Score (Positive review) = 0.16761000000000004
```

FIG. 5B

SYSTEMS AND METHODS FOR PREDICTIVE ANALYSES WITH MACHINE LEARNING SYSTEMS

TECHNICAL FIELD

The present disclosure relates generally to data analytics. More particularly, the present disclosure relates to systems and methods for predictive analytics using learning models adapted for predicting progression of a condition over time.

BACKGROUND

Data analytics are performed in various industries to assist with tasks such as forecasting future conditions, generating recommendations, and others. Data analytics can employ machine learning, which provides numerous advantages including accuracy and the ability to effectively use large amounts of data. While these analytics are versatile and effective, they suffer from drawbacks. For example, it is difficult to acquire data and generate useful machine-recognizable inputs, such as features for a machine learning model.

The present disclosure is directed to overcoming one or more of the above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

The present disclosure addresses the technical problem(s) described above or elsewhere in the present disclosure and improves the state of conventional data analytics techniques. In some embodiments, the present disclosure teaches systems and methods for predictive analytics using a machine learning model adapted to predicting progression of a condition.

In some aspects, the techniques described herein relate to a computer-implemented method including receiving, by one or more processors, a dataset including transition data and factor data, the transition data being associated with progression of a condition from a first stage to a second stage, the factor data being associated with one or more factors that influence progression of the condition from the first stage to the second stage, generating, by the one or more processors, a feature for a machine learning model based on the transition data, generating, by the one or more processors and via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating, by the one or more processors, performance of one or more remedial or analytical actions in response to generating the one or more data objects indicative of the transition prediction.

In some aspects, the techniques described herein relate to a system that includes at least one memory having processor-readable instructions stored therein and at least one processor configured to access the at least one memory and execute the processor-readable instructions to perform operations, the operations including: receiving a dataset including transition data and factor data, the transition data being associated with progression of a condition from a first stage to a second stage, the factor data being associated with one or more factors that influence progression of the condition from the first stage to the second stage, generating a feature for a machine learning model based on the transition data, generating, via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating performance of one or more remedial or analytical actions in response to generating the one or more data objects indicative of the transition prediction.

In some aspects, the techniques described herein relate to a non-transitory computer-readable medium storing a set of instructions that, when executed by at least one processor, cause the at least one processor to perform operations including: receiving a dataset including transition data and factor data, the transition data being associated with progression of a condition from a first stage to a second stage, the factor data being associated with one or more factors that influence progression of the condition from the first stage to the second stage, generating a feature for a machine learning model based on the transition data, generating, via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating performance of one or more remedial or analytical actions in response to generating the one or more data objects indicative of the transition prediction.

It is to be understood that both the foregoing general description and the following detailed description are example and explanatory only and are not restrictive of the detailed embodiments, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

FIG. 2 is a block diagram showing an example of a system for predictive analytics, according to some embodiments of the disclosure.

FIGS. 5A and 5B illustrate an example of analysis of a data source, according to some embodiments of the disclosure.

DETAILED DESCRIPTION

Figure 1:
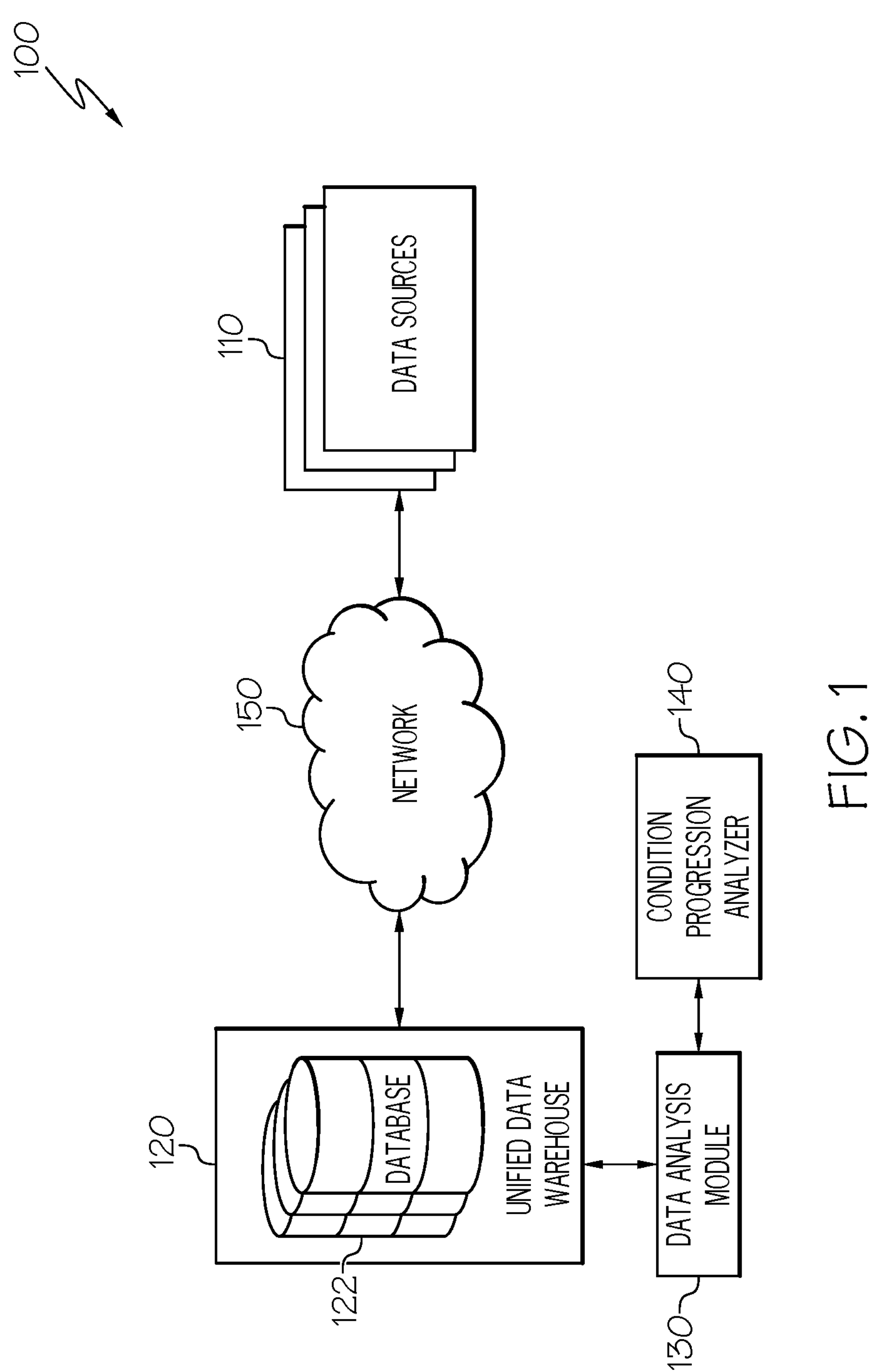
FIG. 1 is a diagram showing an example of a system that is capable of predictive analytics, according to some embodiments of the disclosure.

Various embodiments of this disclosure relate generally to techniques for data analytics, and, more particularly in some embodiments, to systems and methods for predictive analytics using a machine learning model adapted to predicting progression of a condition.

As discussed above, conventional algorithms and models are unable to accurately predict progression of a condition. In particular, conventional automated systems are unable, e.g., due to lack of suitable training data sources, to accurately predict progression of a condition and identify factors that impact whether or not progression is likely to occur.

Techniques disclosed herein may address these technical issues, providing technical improvements over conventional methodology. For example, use of a model trained with structured and unstructured data sources to generate data indicative of transition of a condition may improve prediction accuracy, prediction speed, and identification of factors that impact condition progression. In particular, analysis of unstructured data sources, which can include electronic health records, provide systems and methods with a comprehensive understanding of a subject's condition with reduced reliance on traditional testing methodologies (e.g., blood and/or urine testing). The above technical improvements, and additional technical improvements, will be described in detail throughout the present disclosure. Also, it should be apparent to a person of ordinary skill in the art that the technical improvements of the embodiments provided by the present disclosure are not limited to those explicitly discussed herein, and that additional technical improvements exist.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Various non-limiting embodiments of the present disclosure will now be described to provide an overall understanding of the principles of the structure, function, and use of systems and methods disclosed herein for identifying a problem list section.

Reference to any particular activity is provided in this disclosure only for convenience and not intended to limit the disclosure. A person of ordinary skill in the art would recognize that the concepts underlying the disclosed devices and methods may be utilized in any suitable activity. For example, while some embodiments of the present disclosure are explained in the context of healthcare management, one of ordinary skill would understand the applicability of the described systems and methods to similar tasks in a variety of contexts or environments. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, a "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

Training a machine-learning model may include one or more machine-learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc. After training the machine-learning mode, the machine-learning model may be deployed in a computer application for use on new input data that the machine-learning model has not been trained on previously.

FIG. 1 is a diagram showing an example of a system that is capable of predictive analytics relating to progression of a condition, according to some embodiments of the disclosure. As shown in FIG. 1, an environment 100 facilitates analysis of condition progression, as well as collection, processing, and analysis of relevant data sources. Environment 100 includes data sources 110, a unified data warehouse 120, a data analysis module 130, a condition progression analyzer 140, and a network 150.

In embodiments, various elements of environment 100 communicate with each other through the network 150. While network 150 is shown between data sources 110 and unified data warehouse 120, network 150 may also facilitate communication between data analysis module 130, condition progression analyzer 140, and any of the other elements shown in FIG. 1.

Communication infrastructure of environment 100 supports a variety of different communication protocols and communication techniques. Network 150 of environment 100 includes one or more networks such as a data network, a wireless network, a telephony network, or any combination thereof. It is contemplated that the data network is any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network is, for example, a cellular communication network and employs various technologies including 5G (5th Generation), 4G, 3G, 2G, Long Term Evolution (LTE), wireless fidelity (Wi-Fi), Bluetooth®, Internet Protocol (IP) data casting, satellite, mobile ad-hoc network (MANET), and the like, or any combination thereof.

Data sources 110 include computing systems that are able to generate, modify, and output one or more electronic documents. These electronic documents are associated with factors that can impact whether a condition will progress. In particular, data sources 110 include electronic documents that store dietary information, visit summaries, therapy overviews, discharge summaries, or medical adherence information. These electronic documents include medical records (e.g., electronic health records), and both structured and unstructured data, in at least some embodiments.

These computing systems and/or electronic documents are associated with one or more types of entities, including medical care providers (e.g., hospitals, doctor's offices, urgent care centers, accountable care organizations, etc.), insurance companies, technology providers, governmental agencies, and others. Examples of electronic documents created and/or modified and included in data sources 110 include diet plans or other documents with dietary information (e.g., past dietary habits, data indicating prior adherence to a diet plan, dietary guidelines for future use, etc.), medical visit information (e.g., summaries of visits, visitation dates, visitation frequency data, etc.), therapy overviews (e.g., medical treatments, test results such as blood chemical information, medication information such as currently-prescribed or previously-prescribed medications, etc.), discharge summaries (e.g., notes generated when a patient is discharged from a medical provider following a medical event, check-up appointment, emergency visit, etc.), or adherence information (e.g., characterizations of a patient's past or current level of compliance with directions from a medical provider, adherence to medication instructions, adherence to exercise instructions, etc.). This data can be in narrative form, including subjective information such as notes drafted by a medical professional and objective information such as test scores, including blood test values, diagnoses, currently-prescribed medications, etc.

In addition to the above-described information, data sources 110 may include information such as one or more of: a patient identifier (e.g., medical record number (MRN)), admission and/or readmission data, discharge data, treatment data, patient demographic data (e.g., date of birth, age, residence data, etc.), hospital demographic data, insurance data, authorization data (e.g., insurance prior authorization, etc.), critical care document (CCD) summary data, admission, discharge, transfer (ADT) data, health level seven (HL7) messaging data, insurance claims data, disease indicators (Systematized Nomenclature of Medicine—Clinical Terms (SNOMED), etc.), at least one admission date, readmission date(s), etc.

Unified data warehouse 120 may store one or more of the electronic documents from data sources 110. Data warehouse 120 may include one or more databases 122 that store information from data sources 110. This information may include the electronic documents themselves, as well as information generated by modifying or otherwise processing electronic documents.

The electronic documents of data sources 110 and/or unified data warehouse 120 can take various forms, such as text-based content, tables, spreadsheets, slides, and/or images. These documents can exist in various formats, such as an unstructured data format or a data format that, in at least some electronic documents, is structured and contains metadata or other information that conforms with a data model. Documents of databases 122 are managed and stored on one or more devices within the environment 100, such as local or remote file servers, cloud-based storage services, or other forms of data repositories.

Data analysis module 130 accesses information stored in databases 122. Data analysis module 130 transforms, compresses, trims or otherwise processes and modifies electronic documents to create one or more datasets in databases 122 that conform with a pre-set format, structure, and/or data model. The datasets may be useful as training data for a machine learning model, for example.

Condition progression analyzer 140 is able to receive data from unified data warehouse, directly or via data analysis module 130, as shown in FIG. 1. Condition progression analyzer 140 uses this data as inputs. These inputs are processed as training data, data for extracting and generating features, etc.

FIG. 2 is a block diagram of an environment 200 that corresponds to environment 100 in at least some examples. Environment 200 includes a data analysis module 205, which is an example of data analysis module 130, a condition progression analyzer 260, which is an example of condition progression analyzer 140, and analysis/recommendation outputs 290.

Data analysis module 205 includes a natural language processing (NLP) processor 220 configured to analyze data sources that contain text information, a feature extractor 230, a structured document analyzer 240, and an unstructured document analyzer 250. Condition progression analyzer 260 includes one or multiple machine learning (ML) models. In the illustrated example, condition progression analyzer 260 includes two machine learning models, a clustering machine learning model 272 (e.g., a model that employs hierarchical or k-means techniques) that is part of a clustering system 270, and a predictive machine learning model 282 that is part of predictive system 280. Analysis/ recommendation outputs 290 may be generated with the ML model(s) of condition progression analyzer 260. These outputs 290 may include a probability (e.g., of condition progression), transition metrics (e.g., data impacting a likelihood of condition progression), and/or recommendations or other remedial actions for preventing condition progression, as described below.

Structured and unstructured data sources 210 are included in data analysis module 205 and/or received by data analysis module 205 (e.g., from a unified data warehouse such as warehouse 120 shown in FIG. 1). In the illustrated example, data sources 210 include data types such as physician notes (e.g., documents including narrative text drafted by a physician), visit summaries (e.g., documents including narrative text), diet charts (e.g., documents relating to a diet advised for a subject, a subject's adherence to a particular diet, etc.), electronic health records (e.g., documents that include prior diagnose or diagnostic values, past treatments, treatment plans, current and past medications, etc.), related history (e.g., family history of one or more medical conditions), and user-supplied data (e.g., responses to questionnaires or surveys). Each of these data types can be structured or unstructured. Each type of data associated with data sources 210 can include transition data and factor data. Transition data and factor data are described below in the example of a particular condition, chronic kidney disease (CKD), and progression of CKD from stage 3 (stage 3A or stage 3B) to stage 4. Transition data and factor data are used as training data (training transition data and training factor data), as query data (e.g., an input to a trained model), or both.

In the example of CKD progression, transition data includes blood or urine test values such as creatinine level, albumin level, or other chemical constituents of blood or urine. Transition data includes information that is known to be directly correlated with stages of CKD and can be used as diagnostic criteria. In some examples, transition data also includes patient demographic data, family history of conditions such as CKD, blood sugar level, cholesterol level, and blood pressure.

Factor data includes information that is not used as diagnostic criteria for the condition, CKD in this example. Factor data includes dietary information, visit summaries, therapy overviews, discharge summaries, medical adherence information, and others. This data can be associated with a subject's lifestyle and is not used as diagnostic criteria. In some examples, factor data does not include chemical constituents of blood and does not include chemical constituents of urine.

NLP processor 220 is configured to analyze both structured and unstructured data sources 210. In particular, NLP processor 220 analyzes unstructured data sources using techniques that extract or generate objective data (e.g., numerical values) based on analysis of subjective information, such as a narrative description of a subject's visit to a health care provider, description of a subject's adherence to a diet plan, description of a subject's adherence to a medication schedule, etc. NLP processor 220 is configured to extract factor data, and, if desired, transition data in conjunction with unstructured document analyzer 250.

Example techniques employed by NLP processor 220 include sentiment analysis, named entity recognition, part of speech tagging, emotion detecting, and others. As shown in FIG. 2, these techniques are performed with a sentiment analyzer, a named entity recognizer, a part of speech tagger, and an emotion detector, respectively. Additional techniques of NLP processor 220 include bag of words analysis, term frequency-inverse document frequency techniques, and word embeddings techniques.

The sentiment analyzer is configured to generate a numerical value (e.g., a score) that represents whether the tone of text contained in the document is positive, negative, or neutral. This score is beneficial for quantifying subjective characteristics such as a subject's adherence medical directions. In the example of a diet plan that is processed for CKD progression analysis, the sentiment analyzer of NLP processor 220 generates a score that indicates a level of adherence to a diet plan.

The named entity recognizer is configured to identify and extract named entities present in text of one or more electronic documents. In the example of CKD progression analysis, the named entity recognizer extracts information related to medical history, a treatment plan, past condition progression, etc. The part of speech tagger is also configured to extract information related to medical history, a treatment plan, subject or condition progression, etc., and operates in conjunction with the named entity recognizer, if desired.

The emotion detector is configured to analyze text and identify patterns present in text of an electronic document. In the example of user-supplied data, the emotion detector (and, if desired, the sentiment analyzer) of NLP processor 220 generates information that represents a subject's mental state, which may be analyzed to identify risk factors associated with condition progression.

Feature extractor 230 is configured to extract features from structured and unstructured data sources 210. Feature extractor 230 is configured to use processes including those described for NLP processor 220. As examples, feature extractor 230 employs a bag of words technique (e.g., creating a vocabulary of all words of interest in a narrative or other text and generating a vector of the occurrences of these words), a term frequency-inverse document frequency technique (e.g., weighting the importance of each word in a document by considering how frequently the word appears in the document and how rarely it appears in the entire corpus of other documents), or a word embeddings technique (e.g., use of trained models to transform words into numerical vectors that capture the meanings and relationships between words).

Structured document analyzer 240 is configured to process structured text documents, including documents that include metadata describing types of information stored in the document. Structured document analyzer 240 is configured to tag various types of data contained in the document based on the metadata or other information stored in the document (e.g., data describing other data in the document or data contained in pre-defined field, data cell, etc.).

Unstructured document analyzer 250 is configured to prepare unstructured documents for processing by NLP processor 220. For example, unstructured document analyzer 250 performs optical character recognition, extracts identified text, splits the text into sentences, spell checks words present in the text, etc.

Clustering system 270 is configured to place individual subjects into clusters. In particular, clustering machine learning model 272 is configured with one or more clustering algorithms that identify subjects with similar characteristics. In the example of CKD, initial classifications for clusters correspond to the stage of CKD for each subject. Classifications for clusters can, additionally or alternatively, include likelihood of progression of CKD from a current stage to another stage. Outputs from clustering machine learning model 272 include the groups of subjects that were identified as having similar characteristics. Characteristics useful for the clustering include, in addition to condition stage, lifestyle characteristics, biochemical values (e.g., results of blood or urine analysis), and others. Clustering machine learning model 272 can be a hierarchical machine learning model, a k-means clustering model, or another type of model, as described above.

Predictive system 280 includes a predictive machine learning model 282. Machine learning model 282 is configured to generate data that indicates one or more of: whether a particular subject is likely to transition from a current stage to another stage, a likelihood (e.g., expressed as a percentage) that a particular subject will transition from a current stage to another stage, a timing at which a particular subject is likely to transition from a current stage to another stage (e.g., via survival modeling techniques), identification of factors that increase the likelihood that a particular subject will transition from a current stage to another stage, identification of factors that are responsible for preventing a particular subject from transitioning from a current stage to another stage, and others.

Outputs from predictive machine learning model 282 are received by clustering system 270, and in particular, by clustering machine learning model 272 of clustering system 270. When configured in this manner, outputs from predictive machine learning model 282 are used by clustering machine learning model 272 to place a particular subject (e.g., a new subject) into a cluster. Clustering machine learning model 272 then generates the above-described outputs.

Outputs of condition progression analyzer 260 include results of an analysis and/or recommendations. Analytics include one or more items of data generated with predictive machine learning model 282, as described above. Recommendation outputs of condition progression analyzer 260 are generated with clustering machine learning model 272 and include actions that a subject can take to slow or avoid progression of the condition from a current stage to another stage. These outputs are described in greater detail below with respect to FIG. 4.

Figure 3:
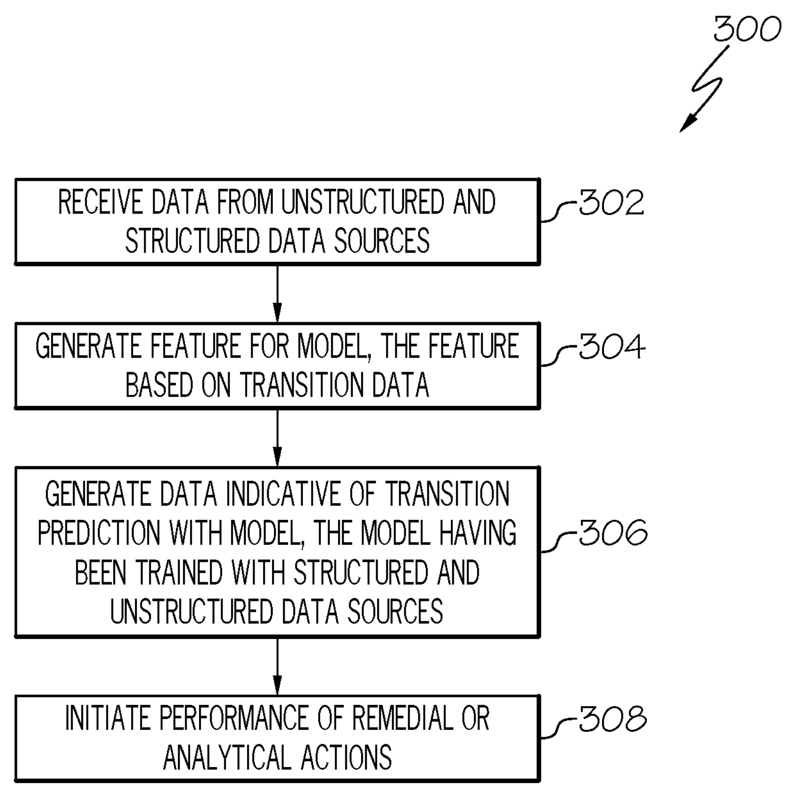
FIG. 3 is a flowchart of an example of a process for predictive analytics, according to some embodiments of the disclosure.
Figure 4:
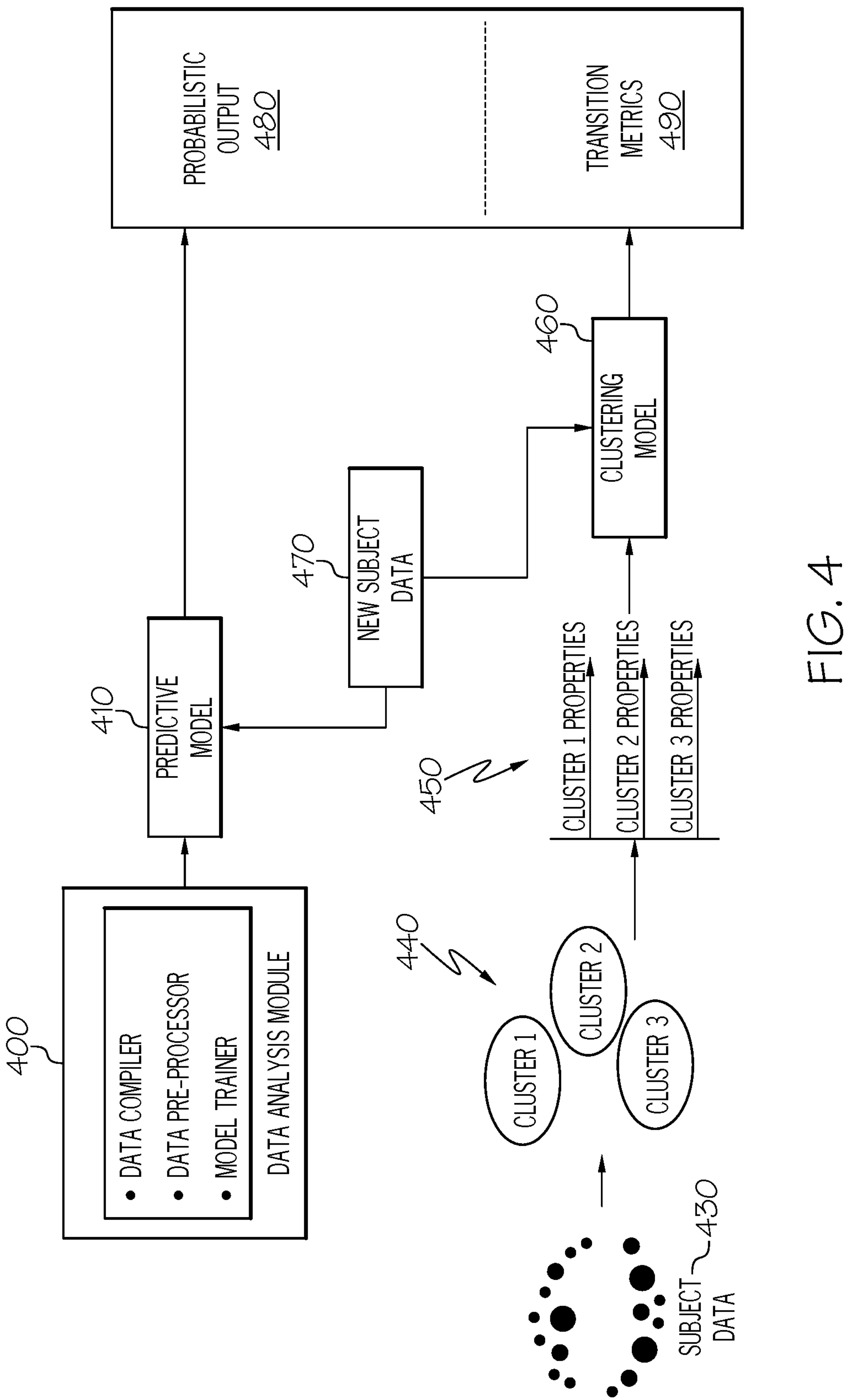
FIG. 4 is a flowchart of an example of a process for predictive analytics, according to some embodiments of the disclosure.

FIG. 3 is a flowchart of an example process 300 for predictive analytics with machine learning systems. FIG. 4, described in conjunction with FIG. 3, is a flowchart corresponding to one or more steps of process 300.

FIG. 4 illustrates a process, with steps or stages that represent datasets, computing systems, machine learning models, and outputs. The process of FIG. 4 is employed to analyze data for a subject, represented by new subject data 470. Part of the process represented in FIG. 4 involves a data analysis module 400 that corresponds to data analysis module 130 and data analysis module 205, a predictive model 410 that corresponds to predictive machine learning model 282, and a probabilistic output 480, one or more data objects, that is an output of predictive model 410. Another part of this process involves subject data 430, one or more datasets that correspond to unified data warehouse 120 and to structured and unstructured data sources 210, a plurality of clusters 440 that each includes one or more subjects, cluster properties 450 that correspond to characteristics associated with each of the clusters 440, a clustering model 460 that corresponds to clustering machine learning model 272, and transition metrics 490, one or more data objects, that is an output of clustering model 460. Probabilistic output 480 and transition metrics 490 each correspond to analysis/recommendation(s) 290 (FIG. 2).

A step 302 of process 300 includes receiving data (e.g., with data analysis module 130 and/or condition progression analyzer 140) from unstructured and structured data sources 210. The unstructured and structured data sources correspond to data stored in unified data warehouse 120 and to structured and unstructured data sources 210. The data is received with data analysis module 400. The data may be received via network 150 and/or by accessing previously-stored data. As indicated in FIG. 2 and described above, the receive data includes physician notes, visit summaries, diet charts, electronic health records, related history documents, and/or user-supplied data.

Data received in step 302 may include subject data 430. Subject data 430 is a dataset that includes characteristics that are associated with particular subjects. The received data also includes new subject data 470, which is data that is input for the purpose of generating probability outputs 480 and/or transition metrics 490.

When desired, step 302 includes analyzing the received data with data analysis module 400. This analysis can be performed before data is received by a machine learning model (e.g., as preprocessing) for use as training data by a machine learning model involved with one or more steps of process 300. The analysis of data in step 302 can be performed for unstructured data and structured data, and includes techniques described with respect to NLP processor 220, structured document analyzer 240, and unstructured document analyzer 250. Suitable NLP processing techniques include sentiment analysis, named entity recognition, part of speech tracking, and emotion detection, as described above with respect to NLP processor 220.

FIGS. 5A and 5B illustrate two respective examples of NLP analyses 500 that can be performed with data analysis module 400 as part of step 302. These analyses 500 can be performed to generate training data for predictive model 410 and clustering model 460, or to generate new subject data 470, including features used to generate outputs 480 and 490.

With reference to FIG. 5A, an NLP analysis of a clinical narrative (e.g., doctor notes or other document including a narrative that does not adhere to a predefined format and/or contain structured data) includes creating an object for sentiment analysis of the clinical narrative, identifying sentences in the narrative, generating a polarity score for each sentence, and calculating an average polarity score for some or all of the sentences. The process may also include extracting data from an unstructured document, for example by processing a document with an optical character recognition algorithm.

NLP analysis 500 in FIG. 5A is performed on a clinical narrative describing a patient that has relatively low adherence to clinical directions. In the example shown in FIG. 5A, an average polarity score 502 is generated by analysis of the narrative, score 502 being about −0.0116. This negative result is generated based on the sentiment analysis of the clinical narrative, without human interpretation or guidance.

NLP analysis 500 in FIG. 5B is performed on a clinical narrative describing a patient that has good adherence to clinical direction. In the example shown in FIG. 5B, an average polarity score 504 is about 0.1676. This positive result is similarly generated based on the sentiment analysis of the clinical narrative.

A step 304 includes generating a feature for a model, such as predictive model 410 and clustering model 460. This feature is based on transition data or other types of data. As described above, examples of transition data include blood or urine test values such as creatinine level, albumin level, or other chemical constituents of blood or urine. Thus, the feature is, at least sometimes, a measurement that is used to define the stage of a condition. In the example of CKD, this feature can be a value used to determine an estimated glomerular filtration rate, or the estimated glomerular filtration rate itself.

Step 304 may also include generating (e.g., with feature extractor 230) a feature based on factor data, instead of or in addition to generating a feature based on transition data. This facilitates, in at least some configurations, the ability to use a non-traditional type of data for generating probabilistic output 480 and/or transition metrics 490. These features can be extracted from the above-described structured or unstructured data. In particular, features can be extracted based on data analyzed with data analysis module 400.

As an example, step 304 includes generating (e.g., with data analysis module 205 and/or condition progression analyzer 260) a score that is used as a feature in a supervised ML model (e.g., predictive model 410 and/or clustering model 460). The score is generated by techniques that include analysis of unstructured data. In particular, the score indicates one or more of: a subject's overall health status, a subject's adherence to a diet plan, a subject's risk factors for transition to a particular stage of a condition, a subject's genetic predisposition to conditions, or a subject's mental state.

The subject's overall health status is calculated by analyzing doctor notes, visit summaries, or other documents with NLP techniques such as named entity recognition and part of speech tagging. Adherence to a diet plan is calculated by use of NLP techniques such as sentiment analysis applied to diet charts or other documents. Risk factors for transition of a condition are calculated by use of NLP or other techniques that identify diagnoses, treatments, and medications included in an electronic health record. Genetic predisposition to conditions is calculated by use of NLP or other techniques to identify family history of chronic conditions included in an electronic health record. Mental state is calculated by use of NLP techniques such as sentiment analysis and emotion detection applied to self-reported data (e.g., questionnaires and surveys) to identify patterns in a subject's mental state.

In the above example, five potential scores are described. Thus, five scores may be determined, each score being used as a feature. If desired, a cumulative or overall score is calculated on the basis of two or more individual scores, the cumulative score being used as a feature.

A step 306 includes generating data indicative of a transition prediction with condition progression analyzer 260. Step 306 can be performed with one, or both, of predictive model 410 and clustering model 460. The data generated includes one, or both, of probabilistic output 480 and transition metrics 490, with the use of clusters 440, and cluster properties 450.

Transition metrics 490 may be generated with clustering model 460, clustering model 460 having been trained based on subject data 430 to generate clusters 440. Each cluster 440 is associated with different cluster properties 450. Cluster properties 450 correspond to characteristics associated with each of the clusters 440, as indicated above. These characteristics include condition stage, lifestyle, chemical constituents of blood or urine, or any factor data described above. Cluster properties 450 are representative (e.g., average or median) values of these characteristics.

Clustering model 460, also having been trained based on subject data 430 (e.g., data compiled with the data compiler, unstructured data processed with the data pre-processor, and the model having been trained with the model trainer), receives new subject data 470 as an input and determines which cluster 440 the new subject belongs to. Based on the identified cluster, clustering model 460 outputs transition metrics 490 that correspond to the relevant cluster properties 450 and to the identified cluster. Transition metrics 490 include numerical values that are expected to represent those of the new subject currently, or numerical values that are expected to approximate those of the new subject when the new subject transitions from the current stage to another stage.

Probabilistic output 480 may be generated with predictive model 410, taking into account the output from clustering model 460. In some aspects, probabilistic output 480 includes a probability (e.g., of condition progression). The probability may be a numerical or qualitative value that represents the risk that the new subject will progress from a current stage of a condition to another stage, such as progression from stage 3 to stage 4 of CKD. The probability may represent a probability that the subject will progress from a current stage to another stage within a certain period of time (e.g., six months, one year, two years, etc.).

In the above-described examples, both probabilistic output 480 and transition metrics 490 represent the current status of the subject (e.g., a cluster 440 in which the subject currently belongs) and metrics associated with a change from the current stage to another stage. In step 308 for initiating performance of remedial or analytical actions, one or both of probabilistic output 480 and transition metrics 490 is displayed, transmitted, etc.

While step 308 may include displaying current status of the subject associated with new subject data 470, step 308 may instead include using probabilistic output 480 and transition metrics 490 to identify one or more proposals, these proposals reducing the likelihood that the new subject progresses from the current stage. For example, transition metrics 490 may identify factors that are expected to have the greatest influence on stage progression for the particular subject represented by new subject data 470 and provide recommendations associated with these factors. For example, if an NLP analysis performed on new subject data 470 reveals a poor adherence to medication schedule as described with respect to FIG. 5A, and clustering model 460 identifies cluster properties 450 that indicate that adherence to medication schedule is a significant factor in stage progression, a recommendation is included in probabilistic output probabilistic output 480 and/or transition metrics 490 for improving this adherence in the future.

In general, any process or operation discussed in this disclosure is understood to be computer-implementable, such as the processes illustrated in FIGS. 3 and 4 are performed by one or more processors of a computer system as described herein. A process or process step performed by one or more processors is also referred to as an operation. The one or more processors are configured to perform such processes by having access to instructions (e.g., software or computer-readable code) that, when executed by one or more processors, cause one or more processors to perform the processes. The instructions are stored in a memory of the computer system. A processor is a central processing unit (CPU), a graphics processing unit (GPU), or any suitable type of processing unit.

A computer system, such as a system or device implementing a process or operation in the examples above, includes one or more computing devices. One or more processors of a computer system are included in a single computing device or distributed among a plurality of computing devices. One or more processors of a computer system are connected to a data storage device. A memory of the computer system includes the respective memory of each computing device of the plurality of computing devices.

Figure 6:
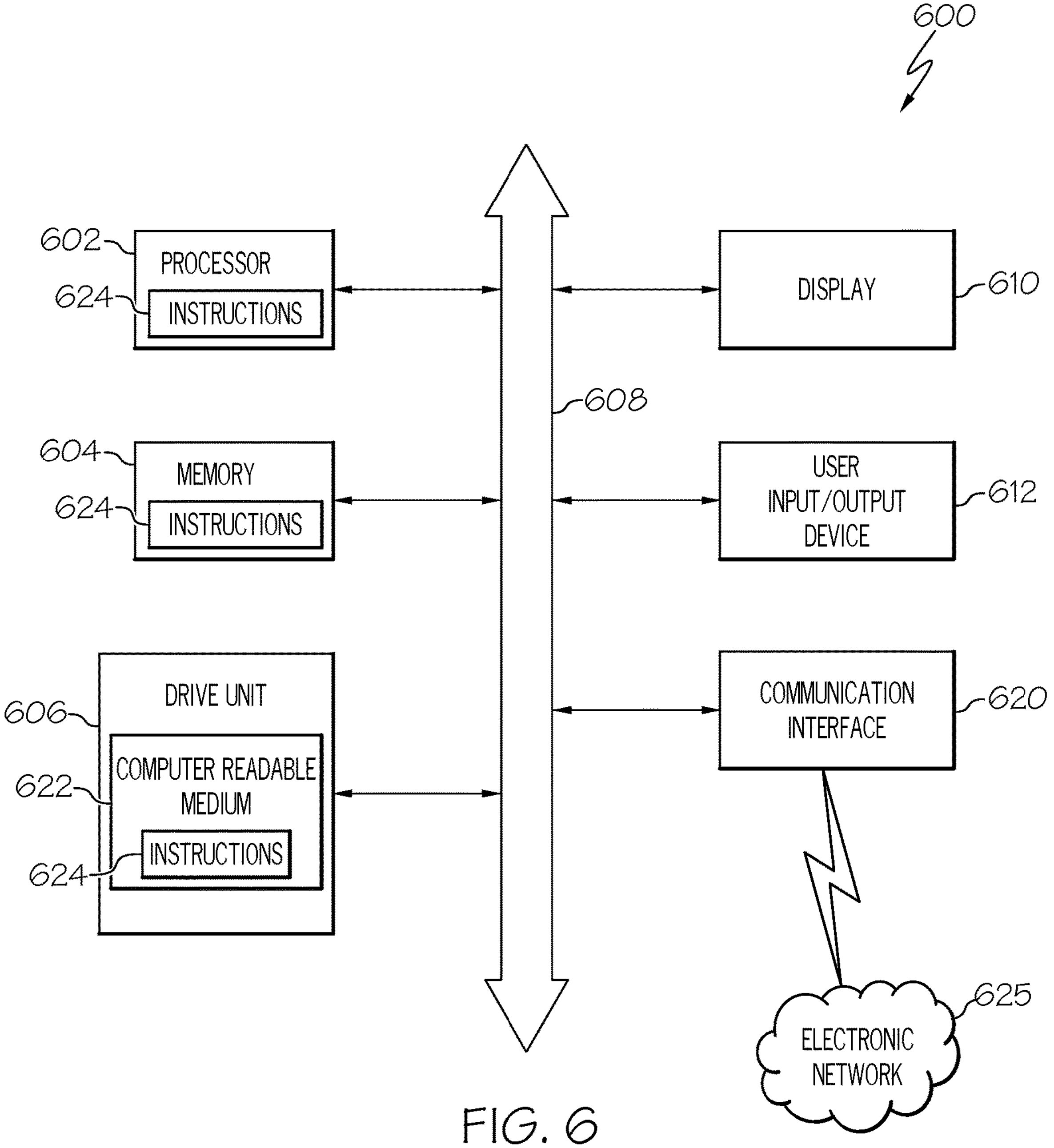
FIG. 6 illustrates an implementation of a computer system that executes techniques presented herein, according to some embodiments of the disclosure.

FIG. 6 illustrates an implementation of a computer system that executes techniques presented herein. The computer system 600 includes a set of instructions that are executed to cause the computer system 600 to perform any one or more of the methods or computer based functions disclosed herein. The computer system 600 operates as a standalone device or is connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" refers to any device or portion of a device that processes electronic data, e.g., from registers and/or memory to transform that electronic data into other electronic data that, e.g., is stored in registers and/or memory. A "computer," a "computing machine," a "computing platform," a "computing device," or a "server" includes one or more processors.

In a networked deployment, the computer system 600 operates in the capacity of a server or as a client user computer in a server-client user network environment, or as a peer computer system in a peer-to-peer (or distributed) network environment. The computer system 600 is also implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 600 is implemented using electronic devices that provide voice, video, or data communication. Further, while the computer system 600 is illustrated as a single system, the term "system" shall also be taken to include any collection of systems or sub-systems that individually or jointly execute a set, or multiple sets, of instructions to perform one or more computer functions.

As illustrated in FIG. 6, the computer system 600 includes a processor 602, e.g., a central processing unit (CPU), a graphics processing unit (GPU), or both. The processor 602 is a component in a variety of systems. For example, the processor 602 is part of a standard personal computer or a workstation. The processor 602 is one or more processors, digital signal processors, application specific integrated circuits, field programmable gate arrays, servers, networks, digital circuits, analog circuits, combinations thereof, or other now known or later developed devices for analyzing and processing data. The processor 602 implements a software program, such as code generated manually (i.e., programmed).

The computer system 600 includes a memory 604 that communicates via bus 608. The memory 604 is a main memory, a static memory, or a dynamic memory. The memory 604 includes, but is not limited to computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 604 includes a cache or random-access memory for the processor 602. In alternative implementations, the memory 604 is separate from the processor 602, such as a cache memory of a processor, the system memory, or other memory. The memory 604 is an external storage device or database for storing data. Examples include a hard drive, compact disc ("CD"), digital video disc ("DVD"), memory card, memory stick, floppy disc, universal serial bus ("USB") memory device, or any other device operative to store data. The memory 604 is operable to store instructions executable by the processor 602. The functions, acts, or tasks illustrated in the figures or described herein are performed by the processor 602 executing the instructions stored in the memory 604. The functions, acts, or tasks are independent of the particular type of instruction set, storage media, processor, or processing strategy and are performed by software, hardware, integrated circuits, firmware, micro-code, and the like, operating alone or in combination. Likewise, processing strategies include multiprocessing, multitasking, parallel processing, and the like.

As shown, the computer system 600 further includes a display 610, such as a liquid crystal display (LCD), an organic light emitting diode (OLED), a flat panel display, a solid-state display, a cathode ray tube (CRT), a projector, a printer or other now known or later developed display device for outputting determined information. The display 610 acts as an interface for the user to see the functioning of the processor 602, or specifically as an interface with the software stored in the memory 604 or in the drive unit 606.

Additionally or alternatively, the computer system 600 includes an input/output device 612 configured to allow a user to interact with any of the components of the computer system 600. The input/output device 612 is a number pad, a keyboard, a cursor control device, such as a mouse, a joystick, touch screen display, remote control, or any other device operative to interact with the computer system 600.

The computer system 600 also includes the drive unit 606 implemented as a disk or optical drive. The drive unit 606 includes a computer-readable medium 622 in which one or more sets of instructions 624, e.g. software, is embedded. Further, the sets of instructions 624 embodies one or more of the methods or logic as described herein. The sets of instructions 624 resides completely or partially within the memory 604 and/or within the processor 602 during execution by the computer system 600. The memory 604 and the processor 602 also include computer-readable media, as discussed above.

In some systems, computer-readable medium 622 includes the set of instructions 624 or receives and executes the set of instructions 624 responsive to a propagated signal so that a device connected to network 625 communicates voice, video, audio, images, or any other data over the network 625. Further, the sets of instructions 624 are transmitted or received over the network 625 via the communication port or interface 620, and/or using the bus 608. The communication port or interface 620 is a part of the processor 602 or is a separate component. The communication port or interface 620 is created in software or is a physical connection in hardware. The communication port or interface 620 is configured to connect with the network 625, external media, the display 610, or any other components in the computer system 600, or combinations thereof. The connection with the network 625 is a physical connection, such as a wired Ethernet connection, or is established wirelessly as discussed below. Likewise, the additional connections with other components of the computer system 600 are physical connections or are established wirelessly. The network 625 alternatively be directly connected to the bus 608.

While the computer-readable medium 622 is shown to be a single medium, the term "computer-readable medium" includes a single medium or multiple media, such as a centralized or distributed database, and/or associated caches and servers that store one or more sets of instructions. The term "computer-readable medium" also includes any medium that is capable of storing, encoding, or carrying a set of instructions for execution by a processor or that causes a computer system to perform any one or more of the methods or operations disclosed herein. The computer-readable medium 622 is non-transitory, and may be tangible.

The computer-readable medium 622 includes a solid-state memory such as a memory card or other package that houses one or more non-volatile read-only memories. The computer-readable medium 622 is a random-access memory or other volatile re-writable memory. Additionally or alternatively, the computer-readable medium 622 includes a magneto-optical or optical medium, such as a disk or tapes or other storage device to capture carrier wave signals such as a signal communicated over a transmission medium. A digital file attachment to an e-mail or other self-contained information archive or set of archives is considered a distribution medium that is a tangible storage medium. Accordingly, the disclosure is considered to include any one or more of a computer-readable medium or a distribution medium and other equivalents and successor media, in which data or instructions are stored.

In an alternative implementation, dedicated hardware implementations, such as application specific integrated circuits, programmable logic arrays, and other hardware devices, is constructed to implement one or more of the methods described herein. Applications that include the apparatus and systems of various implementations broadly include a variety of electronic and computer systems. One or more implementations described herein implement functions using two or more specific interconnected hardware and/or software modules or devices with related control and data signals that are communicated between and through the modules, or as portions of an application-specific integrated circuit. Accordingly, the present system encompasses software, firmware, and hardware implementations.

Computer system 600 is connected to the network 625 (which may correspond to network 150 in FIG. 1). The network 625 defines one or more networks including wired or wireless networks. The wireless network is a cellular telephone network, an 802.10, 802.16, 802.20, or WiMAX network. Further, such networks include a public network, such as the Internet, a private network, such as an intranet, or combinations thereof, and utilizes a variety of networking protocols now available or later developed including, but not limited to TCP/IP based networking protocols. The network 625 includes wide area networks (WAN), such as the Internet, local area networks (LAN), campus area networks, metropolitan area networks, a direct connection such as through a Universal Serial Bus (USB) port, or any other networks that allows for data communication. The network 625 is configured to couple one computing device to another computing device to enable communication of data between the devices. The network 625 is generally enabled to employ any form of machine-readable media for communicating information from one device to another.

The network 625 includes communication methods by which information travels between computing devices. The network 625 is divided into sub-networks. The sub-networks allow access to all of the other components connected thereto or the sub-networks restrict access between the components. The network 625 is regarded as a public or private network connection and includes, for example, a virtual private network or an encryption or other security mechanism employed over the public Internet, or the like.

In accordance with various implementations of the present disclosure, the methods described herein are implemented by software programs executable by a computer system. Further, in an example, non-limited implementation, implementations can include distributed processing, component/object distributed processing, and parallel processing. Alternatively, virtual computer system processing can be constructed to implement one or more of the methods or functionality as described herein.

Although the present specification describes components and functions that are implemented in particular implementations with reference to particular standards and protocols, the disclosure is not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure is implemented using any appropriate techniques for implementing the functionality described herein. The disclosure is not limited to any particular programming language or operating system.

It should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention are practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications are made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects.

Example 1. A computer-implemented method comprising: receiving, by one or more processors, a dataset including transition data and factor data, the transition data being associated with progression of a condition from a first stage to a second stage, the factor data being associated with one or more factors that influence progression of the condition from the first stage to the second stage, generating, by the one or more processors, a feature for a machine learning model based on the transition data, generating, by the one or more processors and via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating, by the one or more processors, performance of one or more remedial or analytical actions in response to generating the one or more data objects indicative of the transition prediction.

Example 2. The computer-implemented method of example 1, wherein the data sources on which the machine learning model has been trained include at least one of structured data sources or unstructured data sources, including documents storing dietary information, visit summaries, therapy overviews, discharge summaries, or medical adherence information.

Example 3. The computer-implemented method of example 2, wherein the data sources were analyzed using a natural language processing technique, the natural language processing technique including one or more of sentiment analysis, named entity recognition, part of speech tagging, or emotion detection.

Example 4. The computer-implemented method of any of examples 1-3, wherein the data sources include clinical narratives, the clinical narratives having been analyzed with a sentiment analysis algorithm.

Example 5. The computer-implemented method of any of examples 1-4, wherein the machine learning model is a first machine learning model and the feature is a first feature, the computer-implemented method further comprising: generating, by the one or more processors and via input of at least a second feature into a second machine learning model, one or more data objects indicative of at least one characteristic of an identified cluster, the second machine model having been trained with data sources including factor data having information other than a chemical constituent of blood.

Example 6. The computer-implemented method of example 5, wherein the one or more remedial or analytical actions are initiated based on the transition prediction and the identified cluster.

Example 7. The computer-implemented method of example 5, wherein the second machine learning model is a clustering model that employs hierarchical or k-means techniques.

Example 8. The computer-implemented method of any of examples 1-7, wherein the transition prediction is a transition from a first stage of chronic kidney disease to a second stage of chronic kidney disease, the first stage of chronic kidney disease being stage 3 (stage 3A or stage 3B) chronic kidney disease and the second stage of chronic kidney disease being stage 4 chronic kidney disease.

Example 9. A system comprises: at least one memory having processor-readable instructions stored therein and at least one processor configured to access the at least one memory and execute the processor-readable instructions to perform operations, the operations including: receiving a dataset including transition data and factor data, the transition data being associated with progression of a condition from a first stage to a second stage, the factor data being associated with one or more factors that influence progression of the condition from the first stage to the second stage, generating a feature for a machine learning model based on the transition data, generating, via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating performance of one or more remedial or analytical actions in response to generating the one or more data objects indicative of the transition prediction.

Example 10. The system of example 9, wherein the data sources on which the machine learning model has been trained include at least one of structured data sources or unstructured data sources, including documents storing dietary information, visit summaries, therapy overviews, or medical adherence information.

Example 11. The system of example 10, wherein the data sources were analyzed using a natural language processing technique, the natural language processing technique including one or more of sentiment analysis, named entity recognition, part of speech tagging, or emotion detection.

Example 12. The system of any of examples 9-11, wherein the data sources include clinical narratives, the clinical narratives having been analyzed with a sentiment analysis algorithm.

Example 13. The system of any of examples 9-12, wherein the machine learning model is a first machine learning model and the feature is a first feature, the operations further comprising: generating, via input of at least a second feature into a second machine learning model, one or more data objects indicative of at least one characteristic of an identified cluster, the second machine model having been trained with data sources including the training factor data having information other than a chemical constituent of blood.

Example 14. The system of example 13, wherein the one or more remedial or analytical actions are initiated based on the transition prediction and the identified cluster.

Example 15. The system of example 13, wherein the second machine learning model is a clustering model that employs hierarchical or k-means techniques.

Example 16. The system of example 13, wherein the transition prediction is a transition from a first stage of chronic kidney disease to a second stage of chronic kidney disease, the first stage of chronic kidney disease being stage 3 (stage 3A or stage 3B) chronic kidney disease and the second stage of chronic kidney disease being stage 4 chronic kidney disease.

Example 17. A non-transitory computer-readable medium storing a set of instructions that, when executed by at least one processor, cause the at least one processor to perform operations comprising: receiving a dataset including transition data and factor data, the transition data being associated with progression of a condition from a first stage to a second stage, the factor data being associated with one or more factors that influence progression of the condition from the first stage to the second stage, generating a feature for a machine learning model based on the transition data, generating, via input of at least the feature into the machine learning model, one or more data objects indicative of a transition prediction for a transition from the first stage to the second stage, the machine learning model having been trained: with data sources including training factor data having information other than a chemical constituent of blood, and to output information associated with a transition prediction, and initiating performance of one or more remedial or analytical actions in response to generating the one or more data objects indicative of the transition prediction.

Example 18. The non-transitory computer-readable medium of example 17, wherein the data sources were analyzed using a natural language processing technique, the natural language processing technique including one or more of sentiment analysis, named entity recognition, part of speech tagging, or emotion detection.

Example 19. The non-transitory computer-readable medium of any of examples 17-18, wherein the data sources include clinical narratives, the clinical narratives having been analyzed with a sentiment analysis algorithm.

Example 20. The non-transitory computer-readable medium of any of examples 17-19, wherein the model is a first model and the feature is a first feature, the operations further comprising: generating, via input of at least a second feature into a second model, one or more data objects indicative of at least one characteristic of an identified cluster, the second machine model having been trained with data sources including the training factor data having information other than a chemical constituent of blood.

What is claimed is:

1. A computer-implemented method comprising:

receiving, by one or more processors of a computing system, a dataset including transition data and factor data, the transition data being associated with progression of a condition from a first stage to a second stage, the factor data being associated with one or more factors that influence progression of the condition from the first stage to the second stage;

generating, by the one or more processors and by a data analysis module, a feature for a machine learning model based on the transition data, the data analysis module comprising:

a feature extractor that identifies the transition data and the factor data based on analyses of structured text documents in the dataset and unstructured documents in the dataset to generate the feature;

a structured document analyzer that processes the structured text documents from the dataset for input into the feature extractor; and an unstructured document analyzer that prepares the unstructured documents from the dataset for processing by a natural language processor for input into the feature extractor;

generating, by the one or more processors and via input of at least the feature into the machine learning model, one or more data objects indicative of a transition prediction for a transition from the first stage to the second stage, the machine learning model having been trained with: (i) data sources including training factor data having information other than a chemical constituent of blood, (ii) previously-generated features extracted by the feature extractor, and (iii) previously-generated transition predictions for the transition from the first stage to the second stage, to output information associated with a transition prediction; and initiating, by the one or more processors, performance of one or more remedial or analytical actions in response to generating the one or more data objects indicative of the transition prediction.

2. The computer-implemented method of claim 1, wherein the data sources on which the machine learning model has been trained include at least one of structured data sources or unstructured data sources, including documents storing dietary information, visit summaries, therapy overviews, discharge summaries, or medical adherence information.

3. The computer-implemented method of claim 2, wherein the data sources were analyzed using a natural language processing technique, the natural language processing technique including one or more of sentiment analysis, named entity recognition, part of speech tagging, or emotion detection.

4. The computer-implemented method of claim 1, wherein the data sources include clinical narratives, the clinical narratives having been analyzed with a sentiment analysis algorithm.

5. The computer-implemented method of claim 1, wherein the machine learning model is a first machine learning model and the feature is a first feature, the computer-implemented method further comprising:

generating, by the one or more processors and via input of at least a second feature into a second machine learning model, one or more data objects indicative of at least one characteristic of an identified cluster, the second machine learning model having been trained with data sources including factor data having information other than a chemical constituent of blood.

6. The computer-implemented method of claim 5, wherein the one or more remedial or analytical actions are initiated based on the transition prediction and the identified cluster.

7. The computer-implemented method of claim 5, wherein the second machine learning model is a clustering model that employs hierarchical or k-means techniques.

8. The computer-implemented method of claim 1, wherein the transition prediction is a transition from a first stage of chronic kidney disease to a second stage of chronic kidney disease.

9. A system, comprising:

one or more processors; and one or more non-transitory computer-readable media storing instructions that, when executed by the one or more processors, cause the one or more processors to perform operations comprising:

receiving a dataset including transition data and factor data, the transition data being associated with progression of a condition from a first stage to a second stage, the factor data being associated with one or more factors that influence progression of the condition from the first stage to the second stage;

generating, by a data analysis module, a feature for a machine learning model based on the transition data, the data analysis module comprising:

a feature extractor that identifies the transition data and the factor data based on analyses of structured text documents in the dataset and unstructured documents in the dataset to generate the feature;

a structured document analyzer that processes the structured text documents from the dataset for input into the feature extractor; and an unstructured document analyzer that prepares the unstructured documents from the dataset for processing by a natural language processor for input into the feature extractor;

generating, via input of at least the feature into the machine learning model, one or more data objects indicative of a transition prediction for a transition from the first stage to the second stage, the machine learning model having been trained with: (i) data sources including training factor data having information other than a chemical constituent of blood, (ii) previously-generated features extracted by the feature extractor, and (iii) previously-generated transition predictions for the transition from the first stage to the second stage, to output information associated with a transition prediction; and initiating performance of one or more remedial or analytical actions in response to generating the one or more data objects indicative of the transition prediction.

10. The system of claim 9, wherein the data sources on which the machine learning model has been trained include at least one of structured data sources or unstructured data sources, including documents storing dietary information, visit summaries, therapy overviews, or medical adherence information.

11. The system of claim 10, wherein the data sources were analyzed using a natural language processing technique, the natural language processing technique including one or more of sentiment analysis, named entity recognition, part of speech tagging, or emotion detection.

12. The system of claim 9, wherein the data sources include clinical narratives, the clinical narratives having been analyzed with a sentiment analysis algorithm.

13. The system of claim 9, wherein the machine learning model is a first machine learning model and the feature is a first feature, the operations further comprising:

generating, via input of at least a second feature into a second machine learning model, one or more data objects indicative of at least one characteristic of an identified cluster, the second machine learning model having been trained with data sources including the training factor data having information other than a chemical constituent of blood.

14. The system of claim 13, wherein the one or more remedial or analytical actions are initiated based on the transition prediction and the identified cluster.

15. The system of claim 13, wherein the second machine learning model is a clustering model that employs hierarchical or k-means techniques.

16. The system of claim 13, wherein the transition prediction is a transition from a first stage of chronic kidney disease to a second stage of chronic kidney disease.

17. One or more non-transitory computer-readable media storing instructions that, when executed by one or more processors, cause the one or more processors to perform operations comprising:

receiving a dataset including transition data and factor data, the transition data being associated with progression of a condition from a first stage to a second stage, the factor data being associated with one or more factors that influence progression of the condition from the first stage to the second stage;

generating, by a data analysis module, a feature for a machine learning model based on the transition data, the data analysis module comprising:

a feature extractor that identifies the transition data and the factor data based on analyses of structured text documents in the dataset and unstructured documents in the dataset to generate the feature;

a structured document analyzer that processes the structured text documents from the dataset for input into the feature extractor; and an unstructured document analyzer that prepares the unstructured documents from the dataset for processing by a natural language processor for input into the feature extractor;

generating, via input of at least the feature into the machine learning model, one or more data objects indicative of a transition prediction for a transition from the first stage to the second stage, the machine learning model having been trained with: (i) data sources including training factor data having information other than a chemical constituent of blood, (ii) previously-generated features extracted by the feature extractor, and (iii) previously-generated transition predictions for the transition from the first stage to the second stage, to output information associated with a transition prediction; and initiating performance of one or more remedial or analytical actions in response to generating the one or more data objects indicative of the transition prediction.

18. The one or more non-transitory computer-readable media of claim 17, wherein the data sources were analyzed using a natural language processing technique, the natural language processing technique including one or more of sentiment analysis, named entity recognition, part of speech tagging, or emotion detection.

19. The one or more non-transitory computer-readable media of claim 17, wherein the data sources include clinical narratives, the clinical narratives having been analyzed with a sentiment analysis algorithm.

20. The one or more non-transitory computer-readable media of claim 17, wherein the model is a first model and the feature is a first feature, the operations further comprising:

generating, via input of at least a second feature into a second model, one or more data objects indicative of at least one characteristic of an identified cluster, the second machine learning model having been trained with data sources including the training factor data having information other than a chemical constituent of blood.

* * * * *